United States Patent [19]

Sparks et al.

[11] Patent Number: 4,850,963
[45] Date of Patent: Jul. 25, 1989

[54] APPARATUS AND METHODS FOR ACHIEVING URINARY CONTINENCE

[75] Inventors: Sam L. Sparks, Alpine; Owen D. Brimhall, West Valley City; Stephen C. Peterson, Salt Lake City; Charles D. Baker, Lehi, all of Utah

[73] Assignee: Utah Bioresearch, Inc., Salt Lake City, Utah

[21] Appl. No.: 191,858

[22] Filed: May 4, 1988

Related U.S. Application Data

[63] Continuation of Ser. No. 872,946, Jun. 11, 1986.

[51] Int. Cl.$^4$ ............................................. A61B 19/00
[52] U.S. Cl. ...................................... 600/29; 128/1.3; 128/899; 128/DIG. 25; 604/55; 604/93
[58] Field of Search ....... 128/1 R, 129, 130, DIG. 25, 128/1.3-1.5, 631, 899; 604/55, 93, 362; 623/1; 600/28-30

[56] References Cited

U.S. PATENT DOCUMENTS

| | | | |
|---|---|---|---|
| 2,628,615 | 2/1953 | Saffir | 604/148 |
| 3,419,008 | 12/1968 | Plishner | 128/346 |
| 3,642,004 | 2/1972 | Osthagen et al. | 128/349 |
| 3,731,670 | 5/1973 | Loe | 128/1 |
| 3,750,194 | 8/1973 | Summers | 3/1 |
| 3,812,841 | 5/1974 | Isaacson | 128/1 |
| 3,841,304 | 10/1974 | Jones | 128/1 |
| 3,939,821 | 2/1976 | Roth | 128/1 |
| 4,364,377 | 12/1982 | Smith | 128/325 |
| 4,599,083 | 7/1986 | Perlov et al. | 623/3 |

OTHER PUBLICATIONS

*Some Applications of Ferrofluid Magnet Colloid,* Kaiser et al., 4/70.

*Primary Examiner*—Dalton L. Truluck
*Assistant Examiner*—Denise Whelton
*Attorney, Agent, or Firm*—Workman, Nydegger & Jensen

[57] ABSTRACT

Methods and apparatus for maintaining urinary continence in normally incontinent individuals. The present invention involves the non-surgical implantation of a bolus of ferromagnetic material into the bladder. The bolus of ferromagnetic material may comprise a biocompatible membrane, containing a ferromagnetic material. The bolus will normally rest at the juncture between the bladder and the urethra and will prevent the flow of urine from the bladder into the urethra. Essentially, the bolus serves as a seal between the urethra and the bladder. When it is desired to void the bladder, the ferromagnetic bolus is moved out of the intersection between the bladder and the urethra by positioning a magnet along the external surface of the person's body and manipulating the magnet until the desired movement of the bolus is accomplished. Movement of the magnet is sufficient to displace the bolus such that flow may be initiated from the bladder into the urethra.

29 Claims, 2 Drawing Sheets

APPARATUS AND METHODS FOR ACHIEVING URINARY CONTINENCE

This application is a continuation application of U.S. application Ser. No. 06/872,946, filed June 11, 1986, for "Apparatus and Methods for Achieving Urinary Continence."

BACKGROUND

1. Field of the Invention

The present invention is related to methods and apparatus for controlling urinary incontinence.

2. Background of the Invention

Urinary incontinence is an extremely widespread problem within the United States and throughout the world. Urinary incontinence affects people of all ages, but is especially common among older people. It is estimated that close to one million Americans are candidates for surgical correction of urinary incontinence through measures such as the implantation of an artificial urinary sphincter. Urinary incontinence has a multiplicity of causes including accidents, disease, or embryonic defect.

Urinary incontinence is a potentially serious condition, both physiologically and psychologically. In older children and in adults the inability to control one's bladder can have severe psychological impacts. In a patient in an otherwise weakened state, such as an aged person, urinary incontinence may affect the person's very will to live. While in such a condition, dealing with urinary incontinence, including the use of diapers and the like, can be devastating to a person's ego and self-image. As a result, it is necessary that methods and apparatus be developed which can effectively and efficiently control urinary incontinence in order to avoid such adverse impacts.

Urinary incontinence is also serious and detrimental to a patient's physical well-being This condition may require surgery, with its associated dangers and traumas, or it may require the use of catheters in treatment. Both alternatives have potential adverse physical effects including tissue damage and infection, as will be discussed below.

The urinary tract comprises a series of components. Initially, blood flows into the kidneys where it is processed through individual kidney nephrons Blood then flows out of the kidney and returns to the general vascular system. Excess water, minerals, and metabolic end products are removed from the blood as it flows through the kidneys. This material is collected and eventually becomes urine.

After urine is formed in the kidney, it exits the kidney through the ureters. Ureters comprise tubes which connect the kidneys with the bladder A pair of ureters, one from each kidney, direct urine flow into the bladder. Thus, urine will continue from the kidneys, through the ureters, and into the bladder. 22 The bladder is in essence a storage vessel for urine. Urine will collect in the bladder until the bladder is relatively distended. Generally, an adult bladder will hold approximately one pint of fluid. Once the bladder is full, it is necessary to void the bladder. When this occurs the interconnection between the bladder and the urethra is opened by the mechanism described below, and urine flows into the urethra. The urethra in turn carries urine out of the body.

Urinary bladder continence is generally attributed to the tonic contraction of the smooth muscle arranged in the bladder neck. This muscle structure forms the so-called internal sphincter. While not a true sphincter, the funnel-like passage formed by this "trigone region" of the bladder and the urethra, effectively prevents urine flow while in the continent state.

Although knowledge of the physiology of the urinary bladder and urethra is incomplete, continence is generally attributed to the internal sphincter. While not a true sphincter the apposition of the tissue of the trigone and proximal urethra form a purse-like closure of the bladder neck. The base of a normally functioning bladder appears to be flat except during micturition (urination). At that time relaxation of several abdominal muscles, principally the pubo-coccygeus, occurs, the bladder falls and the detrusor contracts forming a funnel-like opening at the bladder neck. Vesical pressure increases, due to abdominal contraction as well as the tonus of the bladder wall, and the urine flows into the urethra. Expansion of the urethra produces a reflex action which causes a further increase in the vesicle pressure. This feedback process continues until the bladder is emptied.

In most children older than four years, it is possible for the higher brain centers to prevent actual urination by holding the external sphincter closed after the urge to void is felt. In the micturition sequence, the cortical centers release the neutral excitation and the urethra relaxes to permit urine passage. If the external sphincter is not relaxed, the contracting detrusor muscle can generate pressures high enough to produce tissue damage.

Urinary incontinence occurs when an individual is unable to control the muscle relaxation sequence described above. In incontinent individuals, urine may flow into the urethra regardless of attempts by the individual to control that flow.

In order to control urinary incontinence, many types of devices have been developed. One class of devices essentially constitutes a cuff or similar structure which is surgically implanted around the exterior wall of the urethra. When it is desired to prevent urine flow, the cuff is hydraulically or mechanically closed so that it is positioned tightly around the urethra. Using this type of device the urethra is physically closed by the pressure of the cuff. When it is desired to void the bladder, the external urethra cuff is retracted or relaxed so that the urethra may again open. Once this occurs, urine is free to pass through the urethra and exit the body.

The method of operation of these cuff devices is in direct contrast to the natural method of maintaining continence. The natural method does not involve compressive forces around the exterior of the urethra, but rather the lifting or dropping of the position of the bladder neck. As a result of the unnatural method of operation of these devices, the cuff devices tend to cause severe tissue damage (tissue necrosis) as well as thickening and scaring of the urethra wall. This tissue damage may make it increasingly difficult for the cuff device to effectively close the urethra and for the urethra to reopen when the pressure is released. Because of these problems, cuff devices are only usable for a short period of time before serious difficulties with their use develop. In addition, these devices may become encapsulated during the period of implantation and may fail to properly operate after a relatively short period of time.

It must also be remembered that a contracting detrusor muscle can possibly generate pressures high enough to cause tissue damage. In a bladder capable of reflective contraction, the cuff type artificial sphincter must be used with extreme care since to maintain the continent state in the face of increased vesicle pressure requires a very large compressive force around the urethra. The resulting forces can produce severe tissue damage to the patient. Indeed, with reflexive bladders, it is a common practice to resect the nerves to the external sphincter in order to prevent vesicle tissue damage.

Methods and devices have also been used to physically contract the urethra without using a full cuff. For example, one method involves implanting a cylinder containing a magnet on one side of the urethra external to the urethra. The urethra is then compressed by placing a magnet outside of the body on the distal side of the urethra. As a result, the implanted magnet is forced against the outside wall of the urethra and theoretically contracts or pinches the urethra sufficiently to maintain continence. When it is desired to void the bladder, the external magnet is removed and the forces against the urethra are relaxed, thus allowing urine flow.

This type of device suffers the same disadvantages as those discussed with respect to the cuff. In particular, the constant pressure against the urethra wall may cause severe tissue damage. In addition, the implanted magnet may become encapsulated within the body. Further, it may be difficult to provide magnets powerful enough to effectively compress the urethra over long periods of time in the manner disclosed by this device.

Another approach to controlling incontinence has been to insert an inflatable bulb through the urethra into the bladder. A catheter is permanently attached to the bulb and exits the body through the urethra. When a continent state is desired, the bulb is inflated by means in communication with the external end of the catheter. When it is desired to void the bladder, the bulb is simply deflated such that it no longer blocks the bladder outlet.

There are several problems encountered with the use of this type of device. The most serious problem is that the catheter which exits the body is a direct passageway to the bladder for infection. As a result, it is necessary to continually use antibiotics when this type of device is in place. The antibiotics, in turn, may have serious damaging side effects. As a result, this type of device can only be used for a very short period of time and cannot be used as a long-term treatment of incontinence.

Other types of mechanical devices have been inserted through the urethra into the base of the bladder. These devices are generally mechanically or electrically actuated valves of various descriptions. These valves, however, are quickly encrusted by components of the body fluids which they contact. As a result, they generally fail in a short period of time. In addition, having such valves permanently implanted within the urethra or bladder may cause tissue damage of the type described above.

As a result of the problems discussed above, it is found that many of the existing devices used to control urinary incontinence are not generally usable; or if they are usable, they are usable for only a short period of time. It has been found in the art that a high percentage of devices implanted are prematurely removed because of the problems discussed above. As a result, patients are subjected to the trauma of repeated surgeries without receiving a satisfactory cure for incontinence. It can, therefore, be appreciated that satisfactory methods and apparatus are not presently available for controlling urinary incontinence.

It is apparent that what is needed in the art are methods and apparatus for maintaining urinary continence in normally incontinent individuals. In particular, it would be a significant advancement in the art to provide an apparatus for maintaining urinary continence which was simple, reliable, and not prone to mechanical or electrical failure when implanted within the body. It would also be an advancement in the art if such an apparatus could be implanted and removed nonsurgically. It would be a further advancement in the art to provide an apparatus for maintaining continence which did not significantly damage the tissues of the bladder, urethra, or surrounding areas. It would also be an advancement in the art to provide methods and apparatus for maintaining urinary continence which could do so over extended periods of time. Such methods and apparatus are disclosed and claimed herein.

BRIEF SUMMARY AND OBJECTS OF THE INVENTION

The present invention is related to methods and apparatus for maintaining urinary continence in incontinent individuals. Essentially, the present invention involves the non-surgical implantation of a bolus of ferromagnetic material into the bladder. The ferromagnetic material may be contained within a biocompatible membrane, it may be integral with such a membrane, or it may form the entire bolus.

The bolus incorporating ferromagnetic material will normally rest at the juncture between the bladder and the urethra, generally referred to as the "trigone region" of the bladder or the bladder neck, and will prevent the flow of urine from the bladder into the urethra. In the alternative, the bolus may be held in place by an external magnet.

In its rest position within the trigone region, therefore, the bolus will maintain urinary continence. Essentially, the bolus serves as a simple, yet effective, seal between the urethra and the bladder. Together with the bladder neck, which forms a seat for the bolus, the bolus forms an effective valve at the intersection between the bladder and the urethra.

When it is desired to void the bladder, the bolus containing the ferromagnetic material is moved out of the intersection between the bladder and the urethra. This is accomplished by positioning a magnet along the external surface of the patient's body and manipulating the magnet until the desired movement of the bolus is accomplished. Movement of the magnet is sufficient to displace the bolus such that flow may be initiated from the bladder into the urethra.

One preferred embodiment of the present invention involves forming a closed membrane from a biocompatible material. The biocompatible material may, for example, be comprised of medical grade polyurethane or polytetrafluoroethylene (Teflon ®). The collapsed membrane can then be inserted nonsurgically through a patient's urethra into the bladder. Once it is in place within the bladder, it is filled with a ferromagnetic material, most likely a liquid.

As mentioned above, other embodiments of the invention may accomplish the same results. For example, the membrane itself may be formed of a ferromagnetic material and then be filled with water, saline or other similar liquid. Alternatively, the bolus may comprise a ferromagnetic solid or a bolus of ferromagnetic gel. As a result, it can be seen that a wide range of possibilities exist for producing a bolus having the required ferromagnetic properties.

One method of accomplishing the implantation of the bolus, particularly if the exterior of the bolus comprises a membrane, is to place the empty membrane into the interior of a hollow catheter. The membrane is also placed in communication with a needle or other similar structure disposed within the interior of the hollow catheter. The needle in turn is connected to a deployment catheter which runs through the interior of the insertion catheter. The deployment catheter is connected to a syringe body which remains external to the patient, and which contains a chamber for holding the ferromagnetic fluid.

Once the catheter is inserted through the urethra and is in communication with the interior of the bladder, ferromagnetic material is injected into the membrane by way of the deployment catheter. Once the membrane contains a sufficient quantity of ferromagnetic material, the needle, or other similar injection means, is withdrawn from the membrane leaving the membrane sealed and full of ferromagnetic fluid. In the alternative, if the membrane itself is ferromagnetic, the injected fluid may not necessarily be ferromagnetic.

Once the membrane is properly sealed, the catheter is removed from the patient. Thus, the end result of the procedure is a membrane containing a quantity of ferromagnetic material, or a ferromagnetic membrane containing a fluid, deposited nonsurgically within the interior of the bladder. In the case of a gel bolous, the bolus may be inserted using a similar catheter arrangement. A solid bolus may comprise an epoxy resin formed in situ in the bladder. The position of the bolus within the bladder can then be controlled by the force exerted on the ferromagnetic bolus by a magnetic field external to the body of the patient.

It is expected that the bolus will generally rest over the opening between the bladder and the urethra, particularly when the individual is in the upright position. That is, the bolus will generally reside within the trigone region of the bladder or the bladder neck. While in this general location, the bolus will seal the bladder neck and block the flow of urine from the bladder into the urethra. When it is desired to void the bladder, the magnet may be moved such that the device is displaced from the trigone region of the bladder and flow from the bladder into the urethra is permitted.

It is, therefore, a general object of the present invention to provide methods and apparatus for adequately maintaining continence in incontinent individuals.

It is also an object of the present invention to provide a device for maintaining continence which is not complicated, but which is reliable and not prone to mechanical or electrical failure when implanted within a patient.

It is another object of the present invention to provide methods and apparatus for maintaining continence in incontinent individuals wherein the device can be installed and removed nonsurgically.

It is an additional object of the present invention to provide methods and apparatus for maintaining continence in incontinent individuals without causing significant tissue damage such that the apparatus can be used over extended periods of time.

It is a further object of the present invention to provide methods and apparatus for maintaining continence in incontinent individuals which apparatus can be manipulated and controlled by the patient.

These and other objects and advantages of the present invention will become apparent upon reading the following detailed description and appended claims, and upon reference to the accompanying drawings.

DETAILED DESCRIPTION OF THE PREFERRED EMBODIMENTS

A. Apparatus of the Preferred Embodiments

Figure 1:
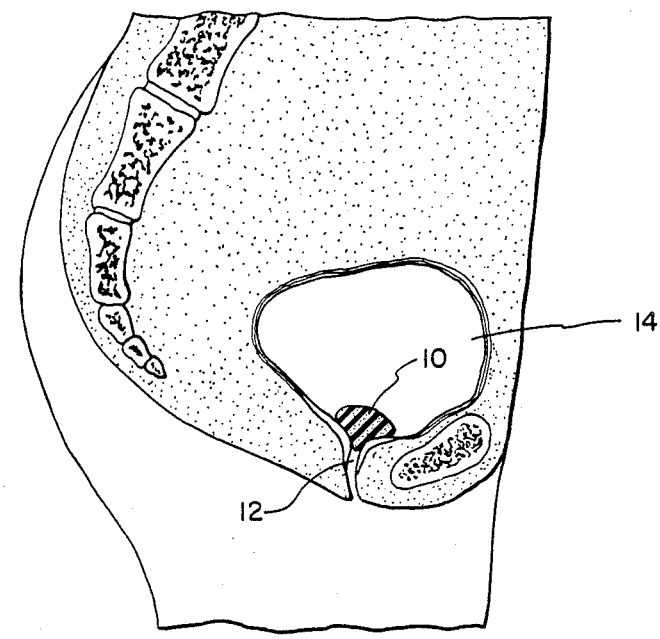
FIG. 1 is a schematic cross-sectional view of the lower abdomen showing the bolus of the present invention inserted within the bladder.

The present invention can be best understood by reference to the drawings, wherein like parts are designated with like numerals throughout. The present invention and its general methods of operation can be understood with reference to FIG. 1. FIG. 1 illustrates the lower abdominal region of the anatomy. Specifically, FIG. 1 illustrates the urethra 12 and the bladder 14.

Also illustrated in FIG. 1 is the bolus 10 of the present invention resting in position within the interior of bladder 14. In one embodiment of the present invention, the bolus includes a membrane formed of biocompatible material. One such biocompatible material is a medical grade polyurethane; however, other various types of material, such as teflon, may also be found acceptable. Materials for constructing the bolus 10 should preferably be biocompatible, non-toxic, and non-lithogenic.

The bolus 10 includes a quantity of ferromagnetic material. The ferromagnetic material may rest within a membrane or it may be integrally formed within the walls of the bolus. Indeed, the ferromagnetic material may be a solid or a gel and may constitute the entire bolus 10.

If the ferromagnetic material is contained within a membrane it will likely be a liquid; however, other materials may also be usable. Various types of ferromagnetic liquids are available. Such liquids may be hydrocarbon-based or may indeed be aqueous-based. One such ferromagnetic liquid is a 900 Gauss saturation ferrofluid manufactured by Ferrofluidics, Inc. Such fluids are preferably non-toxic, biocompatible, chemically stable, and have high magnetic permeability and saturation.

As illustrated in FIG. 1, the bolus 10 is implanted within the interior of bladder 14. Methods of implantation will be discussed in more detail below. When properly in position, bolus 10 will be seated against the interconnection between urethra 12 and bladder 14. This general region is often referred to as the bladder neck or trigone region of the bladder Closure of the trigone region results in the collection of urine within the bladder. As a result, bolus 10, along with the bladder neck essentially comprise a simple, but effective valve for blocking the flow of fluids between bladder 14 and urethra 12. In particular, the bolus 10 is useful in providing continence for normally incontinent individuals.

In order for the bolus 10 to form an adequate seal it is important that it be formed of flexible and compliant material. This allows the bolus to conform to the interior walls of the bladder to effectively prevent fluid flow. Similarly, it may be important that in the case when bolus 10 is a membrane, that the membrane not be filled with fluid to the point that it expands or becomes distended.

Bolus 10 may be manufactured in any acceptable and desirable method. Essentially, all that is necessary is to provide a continuous outer surface of a spherical or other desirable shape. For most purposes a shape which allows for rolling and flexing within the bladder will be preferred in order to facilitate the operation of the device and to minimize encrustation of the bolus 10 with components of the various fluids within the bladder and urethra.

One method of manufacturing such a continuous bolus in the form of a membrane is to first obtain a ball of ice in the desired shape and size. The ball of ice is then dipped into a solution of polymer. One such acceptable polymer is a medical grade polyurethane dissolved in methylene chloride. Once the spherical ball of ice is sufficiently coated with the polymer plastic material, it is removed to a freezer where the polymer is allowed to dry. The dipping and drying procedure may be repeated as necessary to obtain a membrane of the desired thickness. Once the solvent is sufficiently evaporated from the polymer, the ice encapsulated within the resulting polymer membrane can be melted and removed by a small hypodermic needle or by similar other methods.

Alternatively the membrane may be cast on an appropriately shaped conventional mandrel. Once the mandrel is sufficiently coated the membrane may be removed by essentially turning it inside out. Other alternative fabrication methods include blow molding, spray coating, resin casting, and injection moldings.

As mentioned above, the bolus 10 may also comprise a ferromagnetic gel or a ferromagnetic solid. Such a gel would be inserted into the bladder and would operate in the same manner as described above. In the case where the bolus is a solid, the solid may be an epoxy resin which is formed in situ within the bladder.

B. Use of the Preferred Embodiments

Figure 2:
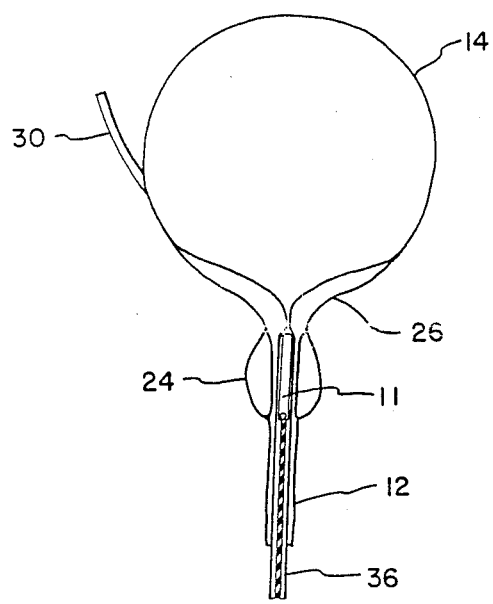
FIG. 2 is a schematic cross-sectional view of a bladder and urethra showing a catheter partially inserted within the urethra.

The methods of using bolus 10 can be clearly understood with reference to FIGS. 2 through 5. FIG. 2 illustrates a bladder 14 and a ureter 30 leading into the bladder 14 from a kidney (not shown). Descending from the base of the bladder 14 is the urethra 12. In addition, FIG. 2 illustrates generally the trigone region 26 of the bladder 14 as well as a prostate gland 24.

Figure 4:
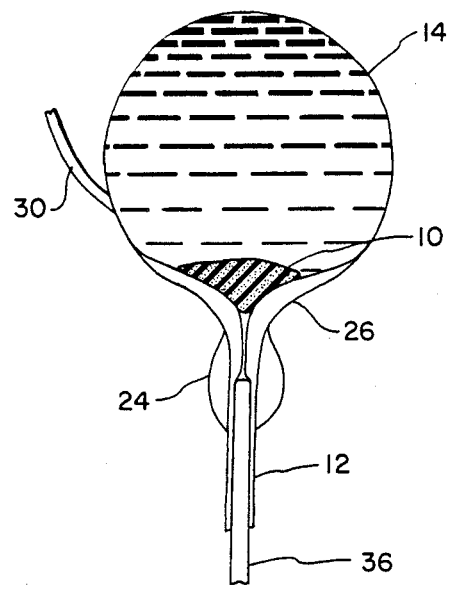
FIG. 4 is a schematic cross-sectional view of a bladder and urethra illustrating the bolus blocking the intersection between the bladder and urethra and the bladder full of urine.
Figure 5:
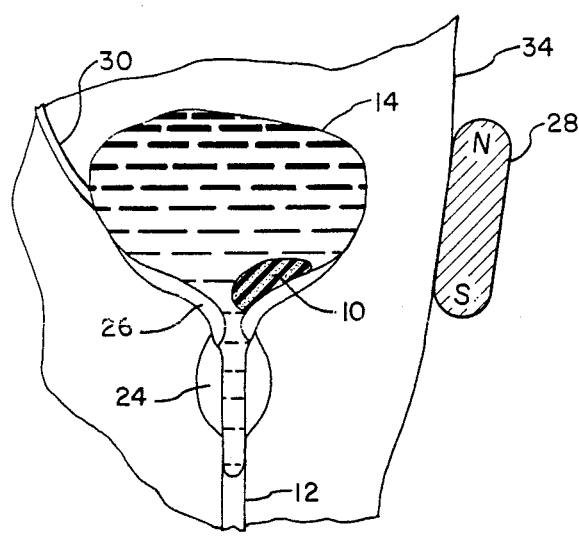
FIG. 5 is a schematic cross-sectional view of a bladder and urethra illustrating the bolus displaced by a magnet and with urine flowing into the urethra.

The operation of the bolus 10 as a seal between bladder 14 and urethra 12 can be fully understood with reference to FIGS. 4 and 5. In FIG. 4, the bolus 10 is shown in place at the base of the bladder 14. In particular, the bolus 10 fully covers the intersection between bladder 14 and urethra 12 in the trigone region 26. Thus, it can be seen in FIG. 4 that urine flowing into the bladder 14 through ureter 30 is collected within the bladder 14 as long as the bolus 10 remains at the base of the bladder 14. FIG. 4 illustrates bladder 14 while relatively distended and full of accumulated urine.

In order to void the bladder 14, it is necessary to remove the bolus 10 from the intersection between bladder 14 and urethra 12, i.e., the bladder neck or trigone region 26. As mentioned above, this is accomplished by positioning a magnet on the skin of the patient in the general vicinity of the bladder 14. FIG. 5 illustrates a magnet 28 positioned outside the skin layer 34 of a patient directly adjacent to the bladder 14. It can be seen that magnet 28 is attracting bolus 10.

To facilitate operation of the invention, it will be appreciated that a sufficiently powerful magnet will be required. One such magnet is a 25 million Gauss-Oersted neodymium-iron-boron magnet sold by The Magnet Store of Castle Rock, Colo. This magnet works well when coupled with the 900 Gauss saturated ferrofluid mentioned above. An appropriate magnet preferably has the properties of being light in weight, being moldable, and having high field strength.

As a result of the action of the magnet 28 on the ferromagnetic material located within bolus 10 or comprising bolus 10, bolus 10 is displaced from the trigone region 26 of the bladder 14 and the intersection between the bladder 14 and the urethra 12 is cleared. In this position urine may flow out of the bladder into urethra 12. This state is fully illustrated in FIG. 5 and will desirably continue until bladder 14 is completely empty.

When bladder 14 is empty, bolus 10 may be reinserted into the trigone region 26 so that urine will again begin to accumulate in bladder 14. Simply removing magnet 28 from the area may be sufficient to allow bolus 10 to drop back into place under the force of gravity In the alternative, magnet 28 may be moved downwardly along the skin of the patient until membrane 10 is again seated within the intersection between bladder 14 and urethra 12.

C. Methods and Apparatus for Implantation

One advantage of the present invention is that the bolus 10 can be inserted and removed nonsurgically. The drawings illustrate one method of such nonsurgical implantation of the bolus, particularly when the bolus comprises a membrane or gel material. In FIG. 2 a urinary insertion catheter 36 is shown travelling upwardly through the urethra 12. The tip of the catheter 36 is at approximately the intersection between the urethra 12 and the bladder 14. Loaded within the interior of the insertion catheter 36 is the membrane 11. It will be appreciated, however, that similar insertion methods could be used to insert a gel bolus. Methods for loading the membrane 11 into the insertion catheter 36 will be described in more detail below.

Figure 3:
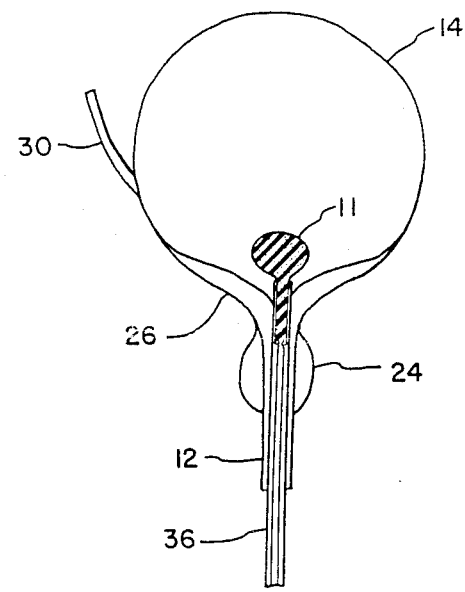
FIG. 3 is a schematic cross-sectional view of a bladder and urethra illustrating a catheter in the process of inserting a bolus into the bladder.

Once the catheter 36 protrudes into the interior of the bladder 14, through the trigone region 26, the membrane 11 is deployed within the bladder 14. FIG. 3 illustrates the membrane 11 being deployed into the bladder and being filled with an appropriate material. This may be a ferromagnetic fluid, or, in the case of a ferromagnetic membrane, the fluid may be non-ferromagnetic.

Figure 6:
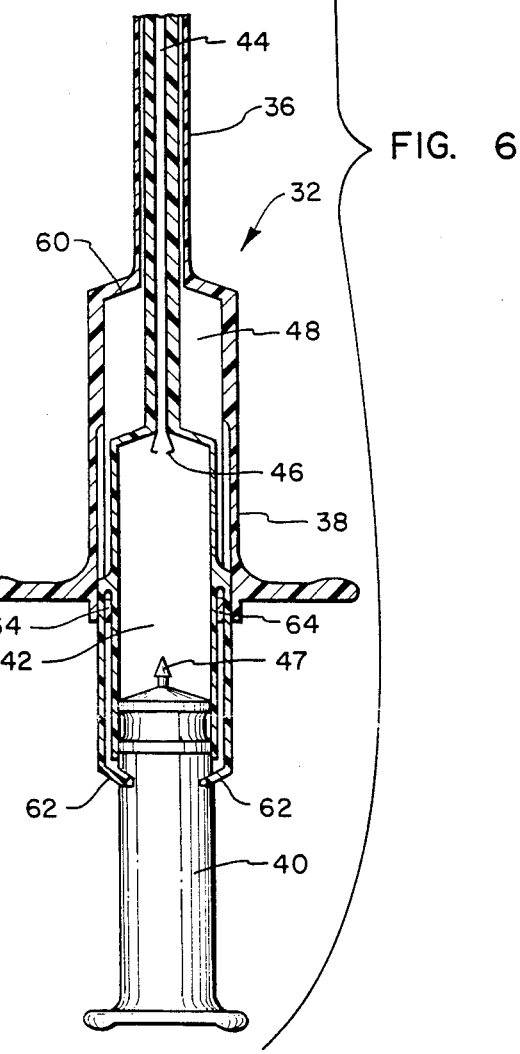
FIG. 6 is a cross-sectional view of one embodiment of an insertion catheter mechanism.

One embodiment of an insertion device or catheter 32 can be understood with reference to FIG. 6. The general catheter assembly 32 includes an insertion catheter 36. Insertion catheter 36 may be, for example, a conventional catheter used in urology.

Insertion catheter 36 is in turn securely attached to a syringe body 38, or other similar device which performs the same general functions. Syringe body 38 includes a plunger ram 40 which runs through the interior of the syringe body 38. Disposed within the interior of the syringe body 38 is reservoir 42. It will be appreciated that prior to use, reservoir chamber 42 is filled with an appropriate amount of ferromagnetic fluid or other appropriate fluid for injection into the interior of the membrane 11 as it is deployed within the interior of bladder 14.

Disposed within the interior of insertion catheter 36 is deployment catheter 44. Deployment catheter 44 runs through the interior of insertion catheter 36 and terminates at its proximal end within the reservoir 42 of syringe body 38. Deployment catheter 44 terminates on its distal end at membrane 11. The distal terminus of deployment catheter 44 is in the form of a needle or other injection means for placing fluid within membrane 11.

On the proximal end of deployment catheter 44, deployment catheter 44 includes a female deployment latch 46. Likewise, the plunger ram 40, which runs through the interior of syringe body 38, contains a male deployment latch 47 which corresponds to the female deployment latch 46 attached to deployment catheter 44. As a result, when plunger ram 40 reaches the end of the ferro-fluid chamber, the male deployment latch 47 of plunger ram 40 will become attached to the female deployment latch 46 of deployment catheter 44. When deployment catheter 44 is secured to the plunger ram 40, plunger ram 40 may be withdrawn slightly resulting in membrane 11 being pushed off the end of deployment catheter 44 as it contacts the distal base 58 of the catheter mechanism or other similar structure within the distal end of deployment catheter 44.

Also illustrated in FIG. 6 is a deployment slide cavity 48. Essentially deployment slide cavity 48 comprises the space between insertion catheter 36 and the reservoir 42 of deployment catheter 44. Deployment catheter 44 is, therefore, relatively free to move within deployment slide cavity 48 and to extend beyond the end of insertion catheter 36 while deploying the membrane 10.

On the distal end of the insertion catheter 36, the membrane 10, is packed within the tip of catheter 36. The distal end of deployment catheter 44 is placed in communication with the interior of the membrane 11 through the septum 50 of membrane 11, if membrane 11 has been fabricated such that it contains a septum.

Figure 7:
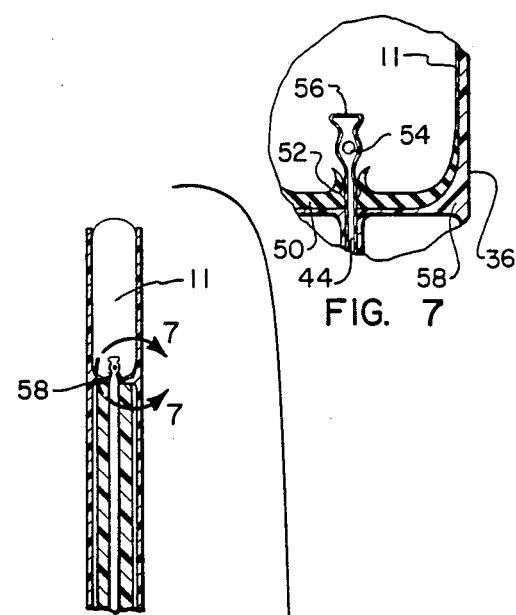
FIG. 7 is a cross-sectional view of one embodiment of the septum portion of a membrane while loaded into the end of the insertion catheter.

The structure of the distal end of the catheter 36, as well as the membrane 11, can be more fully appreciated with reference to FIG. 7. Illustrated in FIG. 7 is the distal end of insertion catheter 36. Disposed within the interior of insertion catheter 36 is deployment catheter 44 Also illustrated in FIG. 7 is the septum area 50 of membrane 11 Membrane 11 may be molded such that a slightly enlarged septum area 50 is disposed on one side of membrane 11.

Disposed through the wall of membrane 11 is an opening 52. Opening 52 may be configured such that it essentially comprises a female joint. At the same time, the distal end of deployment catheter 44 may be configured such that it comprises a male breakaway plug 56. The breakaway plug 56 also contains a filling port 54 through which fluid may be introduced into the interior of membrane 11.

The general method of operation of catheter mechanism 32 can be appreciated with reference to FIGS. 6 and 7. Specifically, the distal end of insertion catheter 36 will be inserted through a patient's urethra 12 into the trigone area of the bladder 14 as shown in FIGS. 2 and 3. Once the tip of insertion catheter 36 reaches the interior of the bladder 14, plunger ram 40 is depressed. This causes the deployment catheter 44, including reservoir 42 and plunger ram 40, to slide within the deployment slide cavity 48. Thus, the membrane 11 is pushed by the distal base 58 of catheter out of the end of insertion catheter 36 and into the bladder.

Once the reservoir 42 contacts the base 60 of insertion catheter 36, latches 62 are directed outwardly by tabs 64, thus releasing plunger ram 40 to enable it to travel within reservoir 42. Fluid contained within reservoir 42 is then pushed by plunger ram 40 through the interior of deployment catheter 44 The fluid flows through the interior of deployment catheter 44 into the interior of membrane 11 through filling port 54 disposed in the distal end of deployment catheter 44.

Once the entire contents of reservoir 42 are pushed through the interior of deployment catheter 44 and out into membrane 11, the male deployment latch 47 on the end of plunger 40 will become lodged within the female deployment latch 46 on the proximal end of deployment catheter 44. At this point in time, membrane 11 will be adequately filled with fluid. Alternatively, the membrane itself may be ferromagnetic and such a membrane may be filled with a non-ferromagnetic fluid. In a third embodiment, a bolus of ferromagnetic gel could be inserted using similar procedures.

Once membrane 11 is filled with fluid and plunger ram 40 is securely locked into the interior of deployment latch 46, the catheter mechanism 32 is ready for removal from the interior of bladder 14. Plunger 40 may, therefore, be withdrawn such that the breakaway septum plug 56 on the distal end of deployment catheter 44 will become lodged in the interior of opening 52 in septum 50. Thus, the opening 52 will be sealed. As the deployment catheter 44 is further pulled away from the membrane 11, the breakaway septum plug will in fact break off of the end of the catheter 44. Further withdrawal of plunger ram 40 results in deployment of membrane 10 within bladder 14 as membrane 11 contacts the distal base 58 and as deployment catheter 44 continues to be withdrawn by pulling on plunger ram 40. At this point, the entire catheter mechanism 32 may be withdrawn from the interior of urethra 12 with membrane 11 left in place within bladder 14.

An alternative to the use of septum plug 56 and opening 52 is simply to place a needle on the end of deployment catheter 44 and to insert the needle into the septum 50. The needle can then be used to fill membrane 11 and can be 22 removed by the same general procedure discussed above. As mentioned above, the septum of the membrane will be constructed such that it is thick enough to seal the interior of membrane 11 once the needle is removed.

This entire procedure will most likely be conducted using ultrasonic imaging, optical cystoscopy, or a fluoroscope so that the position of the various components can be constantly monitored, and such that the bolus 10 is properly disposed within the interior of bladder 14. This procedure when coupled with the use of imaging techniques, however, avoids the need for surgery to correct urinary incontinence. The requirement of surgery to implement existing treatments for urinary incontinence has been a major limitation upon their use and effectiveness.

Since the materials implanted, such as the membrane 11, tend to become encrusted with the components of body fluids, it may be desirable to provide a bolus in which the material within the membrane 11 will be balanced with the fluid outside membrane 11 so that no osmotic pressure gradient is created which would allow material to become imbedded within the wall of the membrane 11.

It may also be necessary to periodically remove bolus 10 from the bladder and replace it with a new bolus due to loss of compliance, leakage, encrustation, infection, or other physiological factors. Removal of membrane 10 is easily accomplished. Where the bolus 10 is a membrane, it is only necessary to insert a urinary catheter having an attached means to puncture the membrane, such as a needle or forceps. The bolus 10 is then punctured and the fluid within the interior of bolus 10 is allowed to escape into the bladder. The fluid immediately flows out the urethra 12. At the same time, bolus 10 may be secured by the catheter and pulled through the interior of urethra 12 to the exterior of the patient. This would also be true using a gel bolus. In the case of a solid bolus it may be necessary to shatter the bolus in order to provide for ready removal from the bladder.

Thus, the bolus 10 can easily be removed and replaced with a new bolus as the need arises. Since neither removal nor replacement requires surgery, such procedures are relatively free of trauma to the patient.

D. Animal Tests

Experiments to test the operation of the device were carried out on an intact dog. A 15 kilogram female dog was anesthetized and placed on her back. The dog was anesthetized to facilitate the experimental procedure. In this position, the bladder neck was somewhat down rather than slightly up as is the normal position in a standing animal. A bolus in the form of a membrane containing ferromagnetic fluid was successfully inserted using the insertion procedure described above. The membrane was filled with a kerosene hydrocarbon-based ferromagnetic fluid and freed from the catheter by the methods described above. The entire procedure was viewed under a fluoroscope such that the proper placement of the membrane could be assured.

This experiment showed that the method of inserting the membrane was very satisfactory and that the membrane could easily be manipulated within the bladder using an external magnet. The animal appeared to be in good condition at the end of the experiment and was found that the dog appeared to be continent.

After approximately eight days, the membrane was ruptured. Examination of the mucosal surface of the bladder showed little inflammation attributable to the device.

In an additional experiment, incontinence was mimicked in a continent dog by inserting an open-tipped catheter far enough into the urethra to penetrate the internal sphincter in the trigone region. The catheter, however, was not inserted far enough into the bladder to prevent the membrane seal from seating in the bladder neck. It was found that by careful manipulation of the membrane bolus within the bladder by an external magnet it was possible to stop and start voiding.

The membrane bolus was left within the dog for six days, at which time nonsurgical removal of the membrane was performed. It was found that the membrane could be emptied by holding the membrane immobile with an external magnet and by nipping the membrane with flexible alligator forceps inserted through a cystoscope. The fluid was then flushed out of the bladder with a saline wash and the deflated membrane bag was secured and removed. Cystoscopic examination of the mucosal surface of the bladder and the membrane itself revealed nothing remarkable. The mucosa was not inflamed and the membrane was intact.

It can be seen, therefore, that the methods and apparatus of the present invention work well in an experimental setting. Actual continence was achieved within an animal with induced incontinence. Likewise, it was found that insertion and removal of the membrane was accomplished with relative ease. Thus, it appears that the methods and apparatus of the present invention actually accomplish each of the objectives set out above without the necessity of surgery.

SUMMARY

In summary, the present invention provides methods and apparatus for maintaining continence in incontinent individuals. This is accomplished by nonsurgically inserting a ferromagnetic bolus into the bladder of such individuals. The bolus may be constructed of a ferromagnetic material or a ferromagnetic fluid may be used to fill the bolus. The bolus is then manipulated by an external magnet to control flow of urine through the bladder. Specifically, a magnet may be used to hold the bolus in place at the intersection between the urethra and the bladder. Alternatively, an external magnet can be used to remove the bolus from the trigone region of the bladder such that a flow of urine will be initiated. All of these manipulations can easily be accomplished directly by the patient. The present invention, therefore, corrects urinary incontinence using inexpensive materials and apparatus and without the need for surgery.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for maintaining urinary continence in incontinent patients, the system comprising:
   a compliant ferromagnetic bolus adapted to be inserted into the urinary bladder of the incontinent patient, said bolus comprising a compliant membrane containing within its interior an aqueous-based fluid, said bolus having a specific gravity greater than that of urine and being capable of seating in the trigone region of the bladder so as to prevent flow of urine into the urethra, and further capable of being selectively moved away from the trigone region to allow the bladder to empty and then again capable of being seated in the trigone region; and
   means adapted to be used at a point external to the body of the incontinent patient capable of magnetically manipulating the position of the bolus within the bladder away from the trigone region, thereby permitting flow of urine into the urethra, and then replacing the bolus within the trigone region to again prevent urine flow into the urethra.

2. A system for maintaining urinary continence as defined in claim 1 wherein the compliant membrane includes a ferromagnetic fluid.

3. A system for maintaining urinary continence as defined in claim 1 wherein the aqueous-based fluid is a ferromagnetic gel.

4. A system for maintaining urinary continence as defined in claim 1 wherein the compliant membrane further includes ferromagnetic particulates.

5. A system for maintaining urinary continence as defined in claim 1 wherein the means for magnetically manipulating the position of the bolus comprises a magnet.

6. A system for maintaining urinary continence as defined in claim 1 wherein the membrane is made of biocompatible material.

7. A system for maintaining urinary continence as defined in claim 1 wherein the membrane is constructed of a polyurethane.

8. A system for maintaining urinary continence as defined in claim 1 wherein the permeability of the membrane and the quantity of ferromagnetic material are chosen such that the fluid pressure within and without the membrane is approximately balanced when the membrane resides within a bladder.

9. A system for maintaining urinary continence as defined in claim 1 wherein the membrane further comprises sealing means for sealing a fluid within the interior of the membrane after said fluid is introduced into the membrane.

10. A system for maintaining urinary continence as defined in claim 9 wherein the sealing means comprises a septum.

11. A system for maintaining urinary continence as defined in claim 1 wherein the aqueous-based fluid is ferromagnetic.

12. A method for controlling urinary incontinence, comprising the steps of:
(a) preparing a closed membrane;
(b) inserting the membrane through the urethra of an incontinent individual into the bladder;
(c) introducing a ferromagnetic material into the membrane;
(d) sealing the membrane so as to minimize flow into and out of the membrane; and
(e) manipulating the position of the membrane and ferromagnetic material therein to open or close the urethral opening to the bladder using a magnet external to the body of the incontinent individual.

13. A method for controlling urinary incontinence as defined in claim 12 wherein the step to inserting the membrane through the urethra comprises:
(i) obtaining a catheter having a syringe body at one end and an insertion catheter at the distal end, the syringe body having a plunger ram and a ferrofluid chamber, the catheter having means for holding a membrane within the distal end of the catheter and means for forcing the membrane out of the end of the catheter;
(ii) placing the membrane within the distal end of the catheter;
(iii) inserting the distal end of the catheter through the individual's urethra into the bladder.

14. A method for controlling urinary incontinence as defined in claim 13 wherein the step of introducing a ferromagnetic fluid into the membrane comprises:

(i) filling the ferrofluid chamber with a predetermined quantity of ferromagnetic fluid;
(ii) placing the distal end of the insertion catheter in communication with the interior of the membrane; and
(iii) sliding the plunger ram into the ferrofluid chamber such that ferromagnetic fluid travels through the insertion catheter into the interior of the membrane.

15. A method for controlling urinary incontinence as defined in claim 14 further comprising the step of forcing the membrane from the end of the insertion catheter such that the membrane is deployed within the bladder.

16. A method for controlling urinary incontinence as defined in claim 15 further comprising the step of removing the catheter from the urethra.

17. A method for controlling urinary incontinence, comprising the steps of:
(a) preparing a closed ferromagnetic membrane;
(b) inserting the membrane through the urethra of an incontinent individual into the bladder;
(c) introducing a fluid into the membrane;
(d) sealing the membrane so as to minimize flow into and out of the membrane; and
(e) manipulating the position of the membrane and ferromagnetic material therein to open or close the urethral opening to the bladder using a magnet external to the body of the incontinent individual.

18. A method for controlling urinary incontinence, comprising the steps of:
(a) preparing a ferromagnetic bolus having a specific gravity greater than that of urine;
(b) inserting the bolus through the urethra or an incontinent individual into the urinary bladder;
(c) manipulating the position of the bolus using a magnet external to the body of the incontinent individual such that the bolus is placed in the trigone region of the bladder in order to close the urethral opening to the bladder; and
(d) further manipulating the position of the bolus away from the trigone region such that urine accumulated in the bladder is free to flow from the bladder, and subsequently manipulating the position of the bolus using said magnet such that the bolus is again placed in the trigone region to again close the urethral opening.

19. A method for controlling urinary incontinence as defined in claim 18 wherein the bolus comprises a ferromagnetic gel.

20. A method for controlling urinary incontinence as defined in claim 18 wherein the bolus comprises a ferromagnetic solid.

21. A method for controlling urinary incontinence as defined in claim 20 wherein the ferromagnetic solid becomes a solid within the bladder.

22. A system for maintaining urinary continence in incontinent patients, the system comprising:
a compliant ferromagnetic bolus adapted to be inserted into the urinary bladder of the incontinent patient, said bolus comprising a compliant ferromagnetic membrane containing a fluid, said bolus having a specific gravity greater than that of urine and being capable of seating in the trigone region of the bladder so as to prevent flow of urine into the urethra, and further capable of being selectively moved away from the trigone region to allow the bladder to empty and then again capable of being seated in the trigone region;

means adapted to be used at a point external to the body of the incontinent patient capable of magnetically manipulating the position of the bolus within the bladder away from the trigone region, thereby permitting flow or urine into the urethra, and then replacing the bolus within the trigone region to again prevent urine flow into the urethra.

23. A system for maintaining urinary continence as defined in claim 22 wherein the means for magnetically manipulating the position of the bolus comprises a magnet.

24. A system for maintaining urinary continence as defined in claim 22 wherein the membrane is made of biocompatible material.

25. A system for maintaining urinary continence as defined in claim 22 wherein the fluid is hydrocarbon based.

26. A system for maintaining urinary continence as defined in claim 22 wherein the is aqueous based.

27. A system for maintaining urinary continence as defined in claim 22 wherein the fluid are chosen such that the fluid pressure within and without the membrane is approximately balanced when the membrane resides within a bladder.

28. A system for maintaining urinary continence as defined in claim 22 wherein the membrane further comprises sealing means for sealing a fluid within the interior of the membrane after said fluid is introduced into the membrane.

29. A system for maintaining urinary continence as defined in claim 28 wherein the sealing means comprises a septum.

* * * * *